US006408847B1

(12) United States Patent
Nuckols et al.

(10) Patent No.: US 6,408,847 B1
(45) Date of Patent: Jun. 25, 2002

(54) REBREATHER SYSTEM THAT SUPPLIES FRESH MAKE-UP GAS ACCORDING TO A USER'S RESPIRATORY MINUTE VOLUME

(76) Inventors: Marshall L. Nuckols, 427 Halsey Rd.; W. Scott Finlayson, 1893 Lindamoor Dr., both of Annapolis, MD (US) 21401

( * ) Notice: Subject to any disclaimer, the term of this patent is extended or adjusted under 35 U.S.C. 154(b) by 22 days.

(21) Appl. No.: 09/652,110

(22) Filed: Aug. 29, 2000

(51) Int. Cl.[7] .............................................. A61M 16/00

(52) U.S. Cl. .............................. 128/204.18; 128/200.24

(58) Field of Search ........................ 128/200.24, 201.26, 128/201.27, 204.18, 204.21, 204.23, 205.11, 205.12, 205.15, 205.17, 205.22, 205.28

(56) References Cited

U.S. PATENT DOCUMENTS 5,619,987 A * 4/1997 Matsuoka .............. 128/204.29
5,678,540 A * 10/1997 Kock .................... 128/205.13
5,924,418 A * 7/1999 Lewis ................... 128/204.22
5,979,443 A * 11/1999 Dingley ................. 128/204.28
6,003,513 A * 12/1999 Readey et al. ......... 128/205.24

* cited by examiner

*Primary Examiner*—Glenn K. Dawson

(57) ABSTRACT

A semi-closed circuit rebreather system that adapts to a user's activity level is provided. A vacuum pressure develops in a chamber coupled to a mouthbit as a breathing gas is drawn by the user from the chamber. A positive pressure develops in the chamber as an exhalation gas is expelled by the user into the chamber. An open circuit is coupled to the chamber to supply an increasing mass of fresh make-up gas to the chamber as vacuum pressure in the chamber develops and increases. A closed circuit coupled to the chamber receives and processes the exhalation gas to produce a recycled gas suitable for breathing. No recycled gas is supplied to the chamber until a threshold vacuum pressure is reached therein. The threshold vacuum pressure is indicative of a higher level of respiratory minute volume (RMV). At that point, a volume of recycled gas is supplied to the chamber proportionally with respect to increases in the mass of fresh make-up gas as vacuum pressure increases beyond the threshold vacuum pressure. Thus, during higher levels of RMV, the recycled gas and fresh make-up gas mix in the chamber prior to inhalation therefrom.

19 Claims, 2 Drawing Sheets

REBREATHER SYSTEM THAT SUPPLIES FRESH MAKE-UP GAS ACCORDING TO A USER'S RESPIRATORY MINUTE VOLUME

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to breathing systems, and more particularly to a semi-closed circuit rebreather capable of supplying fresh make-up gas to a user in accordance with their activity level.

BACKGROUND OF THE INVENTION

Breathing systems are used in a variety of underwater, fire fighting and hazardous material handling applications by the military, scientific and sporting communities. A variety of underwater diving applications are beginning to utilize semi-closed circuit rebreather systems in which fresh make-up gas (i.e., oxygen rich gas) is mixed with the user's exhaled and recycled gas. The advantage of rebreather systems is that they provide for longer bottom times when compared to open circuit SCUBA. A conventional semi-closed circuit underwater breathing apparatus is illustrated in FIG. 1 and is referenced generally by numeral 10.

Apparatus 10 uses a controlled orifice 12 to provide a constant mass injection of fresh make-up gas from a supply 14 into a recycled gas breathing circuit 16. Briefly, recycled gas breathing circuit 16 includes a mouthbit 18 coupled to one of an inhalation bag 20 or an exhalation bag 22 as determined by check valves 24 and 26, respectively. A carbon dioxide scrubber 28 is coupled to bags 20 and 22. In operation, user exhalation causes check valve 24 to close and check valve 26 to open thereby allowing exhaled gas to flow through scrubber 28. During inhalation, check valve 24 opens while check valve 26 closes. Fresh make-up gas as well as gas exiting scrubber 28 are mixed in bag 20 prior to being inhaled by a diver via mouthbit 18. A continuous flow of a mixture of oxygen and nitrogen (or oxygen and helium in deeper applications) is set by orifice 12 to avoid the physiological symptoms of hypoxia and acute oxygen toxicity.

Compared with open circuit, demand-flow underwater breathing apparatus, these semi-closed circuit designs conserve the fresh make-up gas supply which must be carried by the diver. Additionally, the inert gas component in these designs provides the diver with the capability to make deeper excursions than would be possible with closed-circuit, pure oxygen rebreathers.

A disadvantage of this circuit design is that the injection rate for the fresh make-up gas must be set to satisfy the oxygen requirements based on the highest diver activity levels that might be achieved during the dive. Since these injection rates are not coupled with the diver's actual activity level, and consequently his metabolic oxygen consumption rate or respiratory minute volume (RMV) as it is known, this circuit design can experience considerable fluctuations in both circuit oxygen partial pressures and inert gas pressures as the diver's activity changes. The constant injection rate of the fresh make-up gas also creates a considerable risk for hypoxia at high diver metabolic levels in shallow water, or acute oxygen toxicity at low diver metabolic levels at greater depths. In addition, the wide fluctuations in circuit oxygen pressures require decompression schedules that must be tailored to the worse-case inert gas pressures. However, these schedules may be unnecessarily conservative, or even counter-productive, when the circuit inert gas pressures are lower.

SUMMARY OF THE INVENTION

Accordingly, it is an object of the present invention to provide a semi-closed circuit rebreather system that supplies quantities of fresh make-up gas in accordance with changes in a user's respiratory minute volume.

Another object of the present invention is to provide an underwater semi-closed circuit rebreather system that minimizes risks for a diver experiencing a variety of activity levels during a dive.

Still another object of the present invention is to provide an underwater semi-closed circuit rebreather system that provides a constant oxygen volume fraction in the breathing circuit regardless of a diver's activity level.

Other objects and advantages of the present invention will become more obvious hereinafter in the specification and drawings.

In accordance with the present invention, a semi-closed circuit rebreather system has a mouthbit insertable in a user's mouth and a chamber coupled to the mouthbit. A vacuum pressure develops in the chamber as a breathing gas is drawn by the user from the chamber. A positive pressure develops in the chamber as an exhalation gas is expelled by the user into the chamber. First open circuit means are coupled to the chamber for supplying a mass of fresh make-up gas thereto based on pressure in the chamber. The mass of fresh make-up gas is zero when there is positive pressure in the chamber. The mass of fresh make-up gas increases as vacuum pressure in the chamber develops and increases. Second closed circuit means are coupled to the chamber for receiving and processing the exhalation gas to produce a recycled gas suitable for breathing. A volume of the recycled gas is supplied to the chamber based on pressure in the chamber. Specifically, the volume of recycled gas is zero when there is positive pressure in the chamber and when there are only low levels of vacuum pressure in the chamber, i.e., indicative of low RMV. Once a threshold vacuum pressure is reached, a volume of recycled gas is supplied to the chamber and increases proportionally to increases in the mass of fresh make-up gas as vacuum pressure increases beyond the threshold vacuum pressure. Thus, during higher levels of RMV, the recycled gas and fresh make-up gas mix in the chamber prior to inhalation therefrom.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
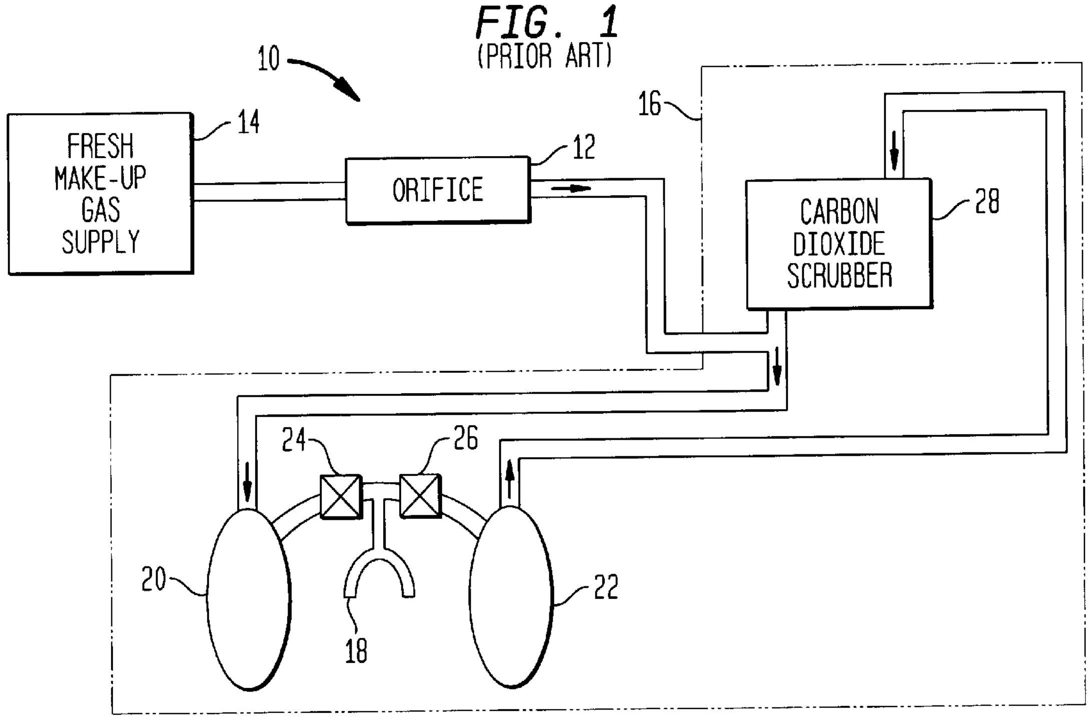
FIG. 1 (PRIOR ART)
FIG. 1 is a block diagram of a semi-closed circuit rebreather system according to the prior art.
Figure 2:
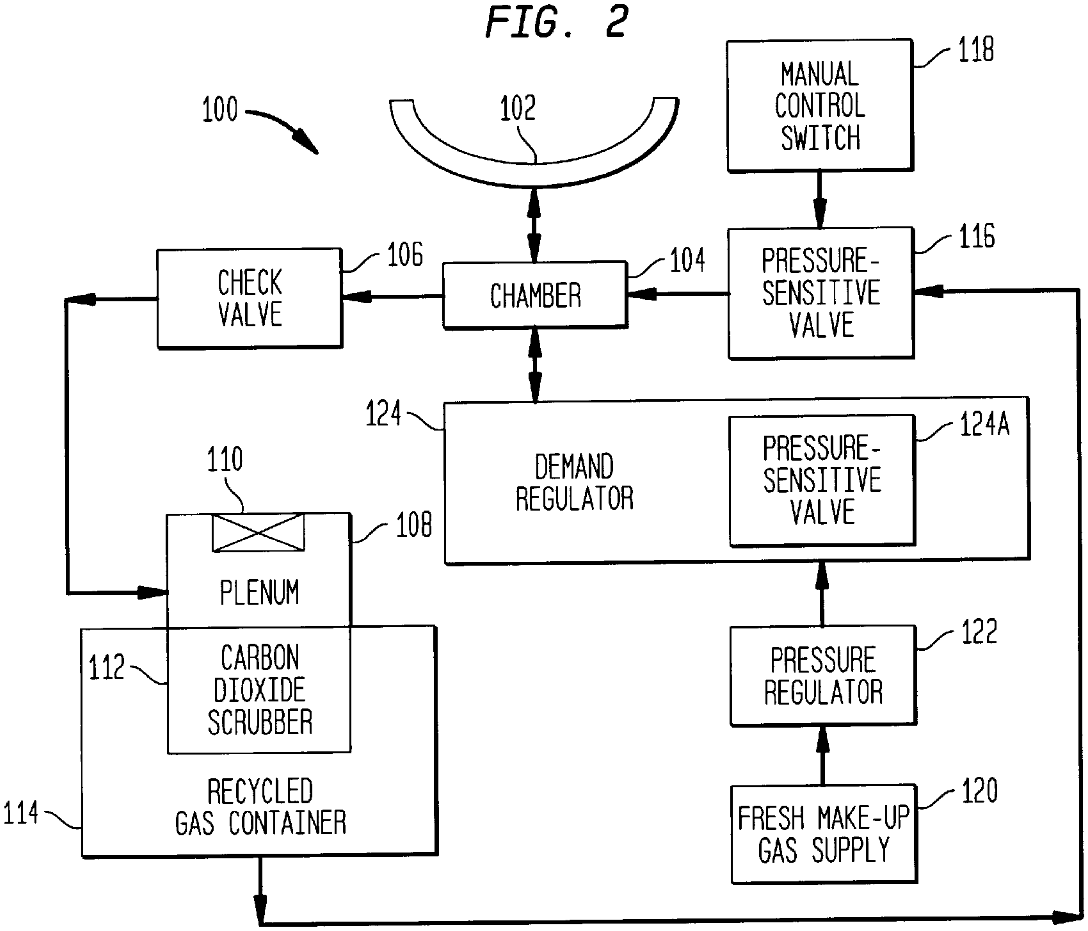
FIG. 2 is a block diagram of a semi-closed circuit rebreather system according to the present invention.

Referring now to the drawings, and more particularly to FIG. 2, a semi-closed circuit rebreather system according to the present invention is shown and referenced generally by numeral 100. Rebreather system 100 will be described with respect to an underwater diving application. However, it is to be understood that rebreather system 100 can also be used in fire fighting and/or hazardous material handling applications.

Rebreather system 100 has a mouthbit 102 that is inserted into a user's mouth. Mouthbit 102, the particular design of which is not a limitation of the present invention, is coupled to a chamber 104 that receives exhalation gas expelled when the user exhales through mouthbit 102, and serves as a source of inhalation gas when the user inhales through mouthbit 102. During exhalation, a positive pressure develops in chamber 104. A negative or vacuum pressure develops in chamber 104 during inhalation. It is the pressure in chamber 104 that governs the flow of gas into and out of chamber 104 as will be explained further below.

Rebreather system 100 uses a closed circuit to recycle a user's exhalation gas and an open circuit to provide the user with fresh make-up gas. With respect to recycling a user's exhalation gas, rebreather system 100 includes a check valve 106 coupled to chamber 104, a plenum 108 coupled to receive the output of check valve 106, an optional pressure relief valve 110 installed in plenum 108, a carbon dioxide scrubber 112 coupled to plenum 108, a compliant recycled gas storage container 114 coupled to scrubber 112, and a pressure-sensitive valve 116 (e.g., a spring-loaded valve) coupled between container 114 and chamber 104. A manual control switch 118 can be coupled to valve 116 to allow a user to keep valve 116 closed thereby making system 100 operate completely in an open circuit mode. For cold environment applications, scrubber 112 can be mounted within container 114 where the warmth of the recycled gas in container 114 improves the performance of scrubber 112.

With respect to supplying a user with fresh make-up gas, rebreather system 100 includes a supply 120 of fresh make-up gas, an absolute pressure regulator 122 coupled to supply 120 for making the fresh make-up gas available at a constant pressure, and a demand regulator 124 having a pressure sensitive valve 124A incorporated therein. Demand regulator 124 is coupled between pressure regulator 122 and chamber 104. Such demand regulators are well known in the art of underwater diving equipment.

As mentioned above, the pressure in chamber 104 at any given time during a user's breathing cycle governs the flow of gas into and out of the chamber 104. A positive pressure in chamber 104 (indicative of the exhalation phase of breathing) causes pressure-sensitive valves 116 and 124A to close and allows check valve 106 to open. A negative or vacuum pressure in chamber 104 (indicative of the inhalation phase of breathing) causes the immediate opening of pressure-sensitive valve 124A and a subsequent opening of pressure-sensitive valve 116. More specifically, pressure-sensitive valve 124A is set to open as soon as any vacuum pressure exists in chamber 104 while pressure-sensitive valve 116 is set to open only after a pre-set level of vacuum pressure (indicative of an increased level of diver activity) is achieved.

During the exhalation phase of a user's breathing cycle, a positive pressure develops in chamber 104 to close valves 116 and 124A and open check valve 106. The exhaled gas flows from chamber 106 to plenum 108 where it is filtered by carbon dioxide scrubber 112 to produce a recycled gas from which carbon dioxide has been extracted. The recycled gas is stored in compliant container 114. When container 114 is filled to capacity, excess exhalation gas is expelled from plenum 108 via pressure relief valve 110.

During the inhalation phase of a user's breathing cycle, a vacuum pressure develops in chamber 104 to close check valve 106 and, at low levels up to the pre-set threshold vacuum pressure, open valve 124A while keeping valve 116 closed. Thus, at low respiratory rates when the user's RMV is low, all inhalation gas is supplied to chamber 104 through valve 124A insuring that the user receives an acceptable level of oxygen-rich fresh make-up gas. The constant pressure of fresh make-up gas provided to valve 124A insures a mass injection rate through valve 124A that is proportional to the inhalation vacuum pressure in chamber 104.

As user activity level increases thereby increasing inhalation demands, the vacuum pressure increases causing valve 124A to open further, i.e., the valve's passage area increases. Then, once the pre-set opening vacuum pressure level of valve 116 is reached, recycled gas from container 114 begins to flow into chamber 104 where it mixes with the fresh make-up gas passing through valve 124A. As the vacuum pressure increases beyond the pre-set threshold pressure, valves 116 and 124A continue to open at proportional rates. Typically, valves 116 and 124A are set to continue opening at the same linear rate in order to maintain a constant required mixing ratio, e.g., a mixing ratio of fresh make-up gas to recycled gas of 1 to 5 is used for a fresh make-up gas oxygen volume fraction of 40 percent. Other mixing ratios would be used when the oxygen volume fraction of the fresh make-up gas is different than 40 percent. Thus, over the full range of respiratory rates, sufficient oxygen will be made available for inhalation to avoid a drop in oxygen partial pressure below the critical level of 0.20 atmospheres.

Figure 3:
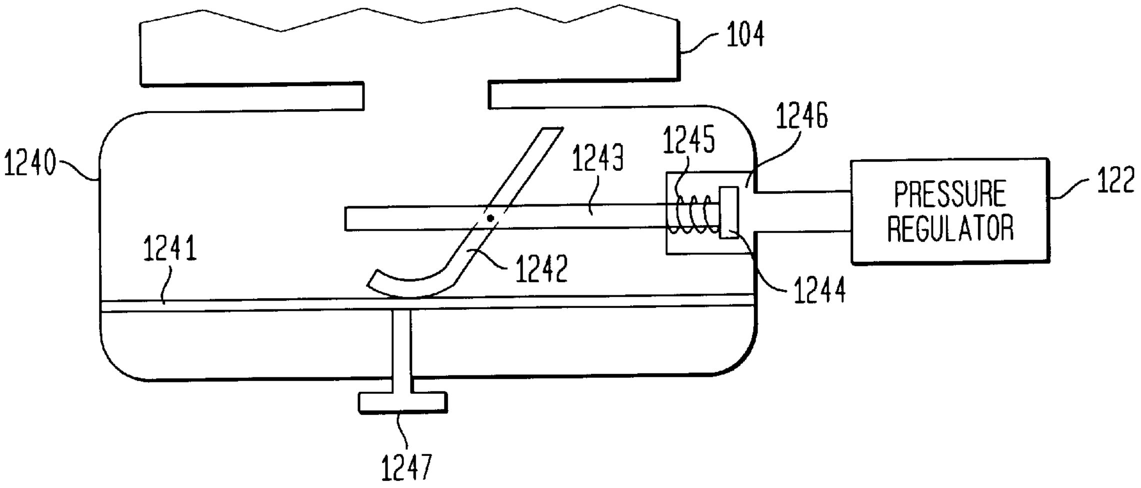
FIG. 3 is a schematic view of a demand regulator incorporating an adjustable pressure-sensitive valve.

As mentioned above, demand regulators incorporating pressure-sensitive valves are known in the art. By way of illustration, one example of a demand regulator that incorporates a pressure-sensitive valve is illustrated schematically in FIG. 3. A housing 1240 supports a diaphragm 1241 exposed to pressure in chamber 104. Vacuum pressure causes diaphragm 1241 to move (upward) against a rocker arm lever 1242 which, in turn, is coupled to a control arm 1243. Control arm 1243 terminates in a valve head 1244 that is biased to a closed or seated position by a spring 1245. Movement of control arm 1243 causes a valve head 1244 to become unseated thereby opening of the valve and allowing fresh make-up gas to enter chamber 104. The greater the vacuum pressure on diaphragm 1241, the greater the movement of control arm 1243 and the greater the open passage area 1246. A manual override button 1247 can be coupled to diaphragm 1241 and/or lever 1242 to allow a user to fully open the valve (regardless of activity level) in order to receive more fresh make-up gas for inhalation.

The advantages of the present invention are numerous. The rebreather system supplies fresh make-up gas in accordance with a user's RMV which is directly related to the user's activity level. Low level respiratory rates are assured sufficient oxygen as only fresh make-up gas is made available for inhalation. As respiratory rates increase, a predetermined mix of recycled and fresh make-up gas is made available for inhalation. The mixture can be set to provide a constant oxygen fraction to mimic an open circuit breathing apparatus while decreasing fresh make-up gas supply requirements.

Figure 4:
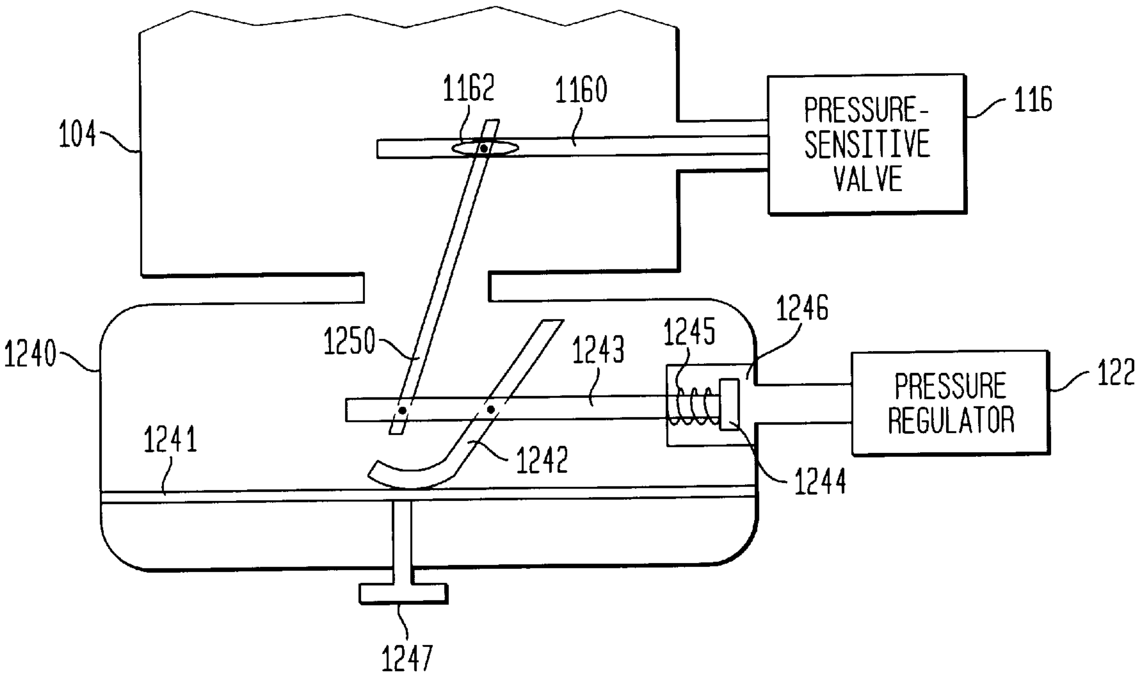
FIG. 4 is a schematic view of an alternative embodiment in which the demand regulator's pressure sensitive valve is mechanically coupled to the recycled gas circuit's pressure sensitive valve.

Although the invention has been described relative to a specific embodiment thereof, there are numerous variations and modifications that will be readily apparent to those skilled in the art in light of the above teachings. For example, the demand regulator's pressure-sensitive valve could be mechanically coupled to valve 116 via a mechanical linkage as illustrated by way of example in FIG. 4. Specifically, control arm 1243 is mechanically linked to a control arm 1160 of valve 116 by a linkage 1250 such that movement of control arm 1160 to open valve 116 occurs only after the predetermined threshold vacuum pressure is achieved in chamber 104. Such delayed movement of control arm 1160 could be controlled by coupling a linkage 1250 to control arm 1160 at a slot 1162 formed in arm 1160. Slot 1162 would permit a certain amount of movement of linkage 1250 (corresponding to vacuum pressures in chamber 104 up to the threshold vacuum pressure) before linkage 1250 and control arm 1160 were fully engaged. At that point, control arms 1243 and 1160 would move together. A variety of other mechanical linkages could be used as would be well understood by one of ordinary skill in the art. It is therefore to be understood that, within the scope of the appended claims, the invention may be practiced other than as specifically described.

What is claimed as new and desired to be secured by Letters Patent of the United States is:

1. A rebreather system, comprising:

a mouthbit insertable in a user's mouth;

a chamber coupled to said mouthbit, wherein a vacuum pressure develops in said chamber as a breathing gas is drawn by the user from said chamber, and wherein a positive pressure develops in said chamber as an exhalation gas is expelled by the user into said chamber;

first means coupled to said chamber for supplying a mass of fresh make-up gas to said chamber based on pressure in said chamber, said mass of fresh make-up gas being zero for said positive pressure and increasing as said vacuum pressure increases; and second means coupled to said chamber for receiving and processing said exhalation gas to produce a recycled gas suitable for breathing, said second means further coupled to said chamber for supplying a volume of said recycled gas to said chamber based on said pressure in said chamber, said volume of said recycled gas being zero for said positive pressure and for low levels of said vacuum pressure up to a threshold vacuum pressure, said volume of said recycled gas increasing proportional to increases in said mass of fresh make-up gas as said vacuum pressure increases beyond said threshold vacuum pressure, wherein said recycled gas and said fresh make-up gas mix in said chamber prior to inhalation therefrom.

2. A rebreather system as in claim 1 wherein said first means comprises:

a supply of fresh make-up gas;

a pressure regulator coupled to said supply for outputting said fresh make-up gas at a constant pressure; and a demand regulator coupled to said pressure regulator and said chamber, said demand regulator having a pressure sensitive valve coupled between said pressure regulator and said chamber, said pressure sensitive valve opening to define a passage when exposed to said vacuum pressure and closing when exposed to said positive pressure, said passage increasing in area proportional to increases in said vacuum pressure.

3. A rebreather system as in claim 2 further comprising means for manually controlling the opening of said pressure sensitive valve.

4. A rebreather system as in claim 2 wherein said second means comprises:

a plenum;

a one-way valve coupled between said chamber and said plenum, said one-way valve opening only when exposed to said positive pressure to pass said exhalation gas to said plenum;

a carbon dioxide scrubber coupled to said plenum for extracting carbon dioxide from said exhalation gas to produce said recycled gas;

a storage container coupled to said carbon dioxide scrubber for storing a supply of said recycled gas; and a second pressure sensitive valve coupled between said storage container and said chamber, said second pressure sensitive valve opening to define a recycled gas passage when exposed to said vacuum pressure above said threshold vacuum pressure and closing when exposed to said positive pressure, said recycled gas passage increasing in area proportional to increases in said vacuum pressure above said threshold vacuum pressure.

5. A rebreather system as in claim 4 wherein said pressure sensitive valve and said second pressure sensitive valve are mechanically coupled to one another.

6. A rebreather system as in claim 1 wherein said second means comprises:

a plenum;

a one-way valve coupled between said chamber and said plenum, said one-way valve opening only when exposed to said positive pressure to pass said exhalation gas to said plenum;

a carbon dioxide scrubber coupled to said plenum for extracting carbon dioxide from said exhalation gas to produce said recycled gas;

a storage container coupled to said carbon dioxide scrubber for storing a supply of said recycled gas; and a pressure sensitive valve coupled between said storage container and said chamber, said pressure sensitive valve opening to define a passage when exposed to said vacuum pressure above said threshold vacuum pressure and closing when exposed to said positive pressure, said passage increasing in area proportional to increases in said vacuum pressure above said threshold vacuum pressure.

7. A rebreather system as in claim 6 further comprising means for manually controlling the closing of said pressure sensitive valve.

8. A rebreather system as in claim 4 wherein said carbon dioxide scrubber is maintained within said storage container.

9. A rebreather system as in claim 4 further comprising a pressure relief valve coupled to said plenum for releasing excess amounts of said exhalation gas therefrom.

10. A rebreather system as in claim 1 wherein said first means operates to provide a linear increase in said mass of fresh make-up gas as said vacuum pressure increases.

11. A rebreather system as in claim 10 wherein said second means operates to provide a linear increase in said volume of recycled gas as said vacuum pressure increases above said threshold vacuum pressure.

12. A rebreather system as in claim 11 wherein said linear increase in said fresh make-up gas increases at the same rate as said linear increase in said recycled gas.

13. A rebreather system, comprising:

a mouthbit insertable in a user's mouth;

a chamber coupled to said mouthbit, wherein a vacuum pressure develops in said chamber as a breathing gas is drawn by the user from said chamber, and wherein a positive pressure develops in said chamber as an exhalation gas is expelled by the user into said chamber;

a supply of fresh make-up gas;

a pressure regulator coupled to said supply for outputting said fresh make-up gas at a constant pressure;

a demand regulator coupled to said pressure regulator and said chamber, said demand regulator having a pressure sensitive valve coupled between said pressure regulator and said chamber, said pressure sensitive valve opening to define a first passage when exposed to said vacuum pressure and closing when exposed to said positive pressure, said first passage increasing in area proportional to increases in said vacuum pressure, wherein a mass of fresh make-up gas is supplied to said chamber based on pressure in said chamber, said mass of fresh make-up gas being zero for said positive pressure and increasing linearly as said vacuum pressure increases;

a plenum;

a one-way valve coupled between said chamber and said plenum, said one-way valve opening only when exposed to said positive pressure to pass said exhalation gas to said plenum;

a carbon dioxide scrubber coupled to said plenum for extracting carbon dioxide from said exhalation gas to produce said recycled gas;

a storage container coupled to said carbon dioxide scrubber for storing a supply of said recycled gas; and a second pressure sensitive valve coupled between said storage container and said chamber, said second pressure sensitive valve closing when exposed to said positive pressure and low levels of said vacuum pressure below a threshold vacuum pressure, said second pressure sensitive valve opening to define a second passage when exposed to said vacuum pressure above a threshold vacuum pressure, said second passage increasing in area proportional to increases in said vacuum pressure above said threshold vacuum pressure, wherein a volume of said recycled gas is supplied to said chamber based on said pressure in said chamber, said volume of said recycled gas being zero for said positive pressure and for said low levels of said vacuum pressure below said threshold vacuum pressure, said volume of said recycled gas increasing linearly with respect to increases in said mass of fresh make-up gas as said vacuum pressure increases beyond said threshold vacuum pressure, wherein said recycled gas and said fresh make-up gas mix in said chamber prior to inhalation therefrom.

14. A rebreather system as in claim 13 wherein linear increases in said fresh make-up gas and said recycled gas occur at the same rate.

15. A rebreather system as in claim 13 wherein said pressure sensitive valve and said second pressure sensitive valve are mechanically coupled to one another.

16. A rebreather system as in claim 13 wherein said carbon dioxide scrubber is maintained within said storage container.

17. A rebreather system as in claim 13 further comprising a pressure relief valve coupled to said plenum for releasing excess amounts of said exhalation gas therefrom.

18. A rebreather system as in claim 13 further comprising means for manually controlling the opening of said pressure sensitive valve.

19. A rebreather system as in claim 13 further comprising means for manually controlling the closing of said second pressure sensitive valve.

* * * * *